(12) United States Patent
Murayama

(10) Patent No.: US 6,475,956 B1
(45) Date of Patent: Nov. 5, 2002

(54) FLOWER-OPENING PROMOTING AGENT FOR PLANTS

(75) Inventor: Akira Murayama, Saga (JP)

(73) Assignee: Ajinomoto Co., Inc., Tokyo (JP)

(*) Notice: Subject to any disclaimer, the term of this patent is extended or adjusted under 35 U.S.C. 154(b) by 0 days.

(21) Appl. No.: 09/696,967

(22) Filed: Oct. 27, 2000

(30) Foreign Application Priority Data

Nov. 2, 1999 (JP) ............................................. 11-312074

(51) Int. Cl.$^7$ ................................................ A01N 43/90
(52) U.S. Cl. ............................................................. 504/241
(58) Field of Search ........................................ 504/241

(56) References Cited

U.S. PATENT DOCUMENTS

| | | | | |
|---|---|---|---|---|
| 3,049,536 A | * | 8/1962 | Reiff et al. ............... | 260/211.5 |
| 5,211,738 A | | 5/1993 | Sasaki et al. ............... | 504/241 |
| 6,143,695 A | | 11/2000 | Murayama .................. | 504/241 |

FOREIGN PATENT DOCUMENTS

| | | |
|---|---|---|
| EP | 0 508 777 | 10/1992 |
| EP | 0 841 007 | 5/1998 |
| JP | 48-26517 | 4/1973 |
| JP | 48-56759 | 8/1973 |

OTHER PUBLICATIONS

Patent Abstracts of Japan, AN 1989–282516 (39), JP 01–207209, Aug. 21, 1989.
Patent Abstracts of Japan, AN 1974–59229V (33), JP 49–027798, Jul. 20, 1974.
Yutaka Ito, et al., STN Chemical Abstracts, AN 85:42078, vol. 7, No. 85, Aug. 16, 1976, "Studies on the Physiological Responses of Crop Plants Following Application of Exogenous Nucleic Acid Components", vol. 20, No. 1, 1975.
Chemical Abstracts, vol. 25, No. 114, AN 114:242821, Jun. 24, 1991, CN 1045683, Oct. 3, 1990.

* cited by examiner

*Primary Examiner*—S. Mark Clardy
(74) *Attorney, Agent, or Firm*—Oblon, Spivak, McClelland, Maier & Neustadt, P.C.

(57) ABSTRACT

Herein is disclosed an excellent flower-opening promoting agent for plants which agent comprises inosine as the effective ingredient, and a method of promoting the opening of flowers with the promoting agent.

21 Claims, No Drawings

FLOWER-OPENING PROMOTING AGENT FOR PLANTS

BACKGROUND OF THE INVENTION

1. Technical Field of the Invention

The present invention relates to a flower-opening promoting agent for plants, more particularly to a flower-opening promoting agent for plants which comprises inosine as the effective ingredient, and a method for promoting the opening of flowers which method comprises the step of applying inosine as the effective ingredient to a plant.

2. Prior Art

Heretofore, several examples in which a nucleic acid-related substance is applied to plants are known.

For example, (a) Japanese Patent Publication (Kokoku) No. 22919/1964 discloses a plant growth regulator comprising, as the effective ingredients, β-indoleacetic acid or the like and at least one substance selected from the group consisting of purine bases, pyrimidine bases, nucleosides and nucleotides obtainable by decomposing nucleic acid.

In the above plant growth regulator, however, the nucleic acid bases, nucleosides and nucleotides obtainable by decomposing a nucleic acid and different in decomposition degree are regarded as substances having the same effects (equivalents) without being distinguished from each other. As is apparent from the disclosure therein that these decomposition products of a nucleic acid except some products belonging to purine bases do not have substantial plant growth regulating action, the plant growth regulator is a composition wherein the combined use of a decomposition product of a nucleic acid and β-indoleacetic acid or the like is an essential requirement.

(b) Japanese Patent Publication (Kokoku) No. 16310/1974 discloses a growth regulator for fruit vegetables comprising, as the effective ingredients, a plant hormone such as chlorophenoxyacetic acid or the like and at least one substance selected from the group consisting of non-decomposed nucleic acid, and pyrimidine bases, purine bases, nucleosides and nucleotides, the last four being obtainable by decomposing nucleic acid.

In this growth regulator for fruit vegetables, however, non-decomposed nucleic acid per se and various decomposition products thereof different in decomposition degree are put in the same category, and besides, as is apparent from the disclosure therein that these nucleic-acid related substances are used in order to reduce the generation of various physiological disorders of crops caused by the application of the aforementioned plant hormone and to increase the expected effects to be brought by the application of the plant hormone, the combined use of a plant hormone and a nucleic-acid related substance is an essential requirement.

(c) Japanese Patent Publication (Kokoku) No. 17670/1979 discloses a method for improving the leaf life of a foliage plant, comprising bringing the leaves, the leaf stems, or the cut ends of petioles of a matured foliage plant into contact with one or more of nucleotides and nucleosides (inosine being given as an example).

Also in the above method for improving the leaf life of a foliage plant, however, various nucleotides and nucleosides are put in the same category and the purpose of improving the leaf life of a foliage plant is obviously different from the purpose of flower-opening promotion according to the present invention.

(d) Japanese Patent Application Laid-Open (Kokai) No. 26517/1973 discloses a method for promoting the germination of pollen of a fruit tree comprising the step of applying a single solution of one of nucleotides, nucleosides (inosine being given as an example) and nucleic acid bases, or a mixed solution of at least two thereof to the flower buds of the fruit tree at its bud stage.

Also in the above method for promoting the germination of pollen of a fruit tree, however, various nucleotides and nucleosides are put in the same category and, in addition, the purpose of promoting the germination of pollen of a fruit tree is obviously different from that of the present invention.

(e) Japanese Patent Laid-Open (Kokai) No. 68848/1975 discloses a method for prolonging the life of cut flowers, comprising using a mixed solution of inosine and calcium chloride (as an aqua used for natural or fresh flowers at a flower shop or an aqua for pouring into a flower bowl or vase) for natural or fresh flowers.

In the above method for prolonging the life of cut flowers, however, the combined use of inosine and calcium chloride is an essential requirement and moreover, the purpose of prolonging the life of cut flowers is obviously different from the purpose of flower-opening promotion according to the present invention.

As has been described above, the use of nucleic-acid related substances for plants has been hitherto known, but the combined use of these substances with other substance is the essential requirement therein. Even if various nucleic-acid related substances are used singly, they are regarded as substances having the same effects (equivalents) without being distinguished from each other. In addition, the purpose of the application of the effective ingredients is obviously different from that of the present invention.

Bt the way, with regard to flower bud formation, the uracil-proline theory proposed by Tatsuji Kobayashi, a one-time assistance professor at Kyoto University, is famous. The theory is based on a result of investigating rice plants, and its content is that there is concentrated accumulation of uracil that is a pyrimidine-type nucleic acid base and proline that is a special amino acid at the flower bud formation. Nobody objects to the participation of nucleic acid components at the flower bud formation apart from proline. On the other hand, however, there still remains a question why uracil is focused. It is difficult to understand that he has paid his attention to uracil, not adenine or guanine of purine-type among nucleic acid bases.

It is, however, not the case that uracil has come into wide use as an agricultural material in the agricultural field. Only at laver cultivation, a part of laver farmers have privately used it, but the results vary widely and its use costs much owing to the high purchase unit price, so that it is not so widely used.

The description and data reported by a one-time assistance professor Mr. Kobayashi show as follows: (a) At metabolism in a rice plant, proline is accumulated in a larger amount than the other amino acids at the time of flower bud formation and the grain appearing stage; (b) Proline is remarkably taken into high molecular weight proteins at reproductive phase stage as compared with at vegetative growth stage; (c) In the nucleic acid metabolism, uracil and cytosine are taken into high molecular weight nucleic acids at a higher rate than adenine and proline are at reproductive phase stage; and (d) As a result of additional fertilization with a mixed solution of uracil and proline every five days from three weeks before the expected coming into ear of a rice plant, a grain increasing effect reaches twice as high as that in the control plot where a mineral fertilizer was alone applied.

The point to notice in connection with the description and data reported by the one-time assistance professor Mr. Kobayashi is that only nucleic acid bases were examined and any nucleoside such as inosine and the like was not an object of the examination nor analysis.

SUMMARY OF THE INVENTION

[Problems to be Solved by the Invention]

If a fruit tree blossoms in a sound and complete state, this leads to larger fruits borne through fertilization of the blossoms and fructification, and as a result, larger and better fruits can be harvested. Also, in the case of natural or fresh flowers, formation of natural flowers capable of being promoted in the bloom-opening and that of blooming flowers of larger and better quality will afford a large profit to cultivating and shipping persons of natural flowers.

Therefore, it is desired to develop a flower-opening promoting agent for plants and a method for promoting the opening of flowers capable of answering such object, and thus, the present invention aims to provide such a flower-opening promoting agent for plants and such a method for promoting the opening of flowers.

[Means for Solving the Problems]

As a result of extensive studies for attaining the above object, the present inventors have found that among nucleic acid-related substances such as nucleic acid bases, nucleosides, nucleotides, and the like, particularly inosine shows such an effect of promoting the opening of flowers. Based on such findings, the invention has been completed.

Accordingly, the present invention relates to a flower-opening promoting agent for plants which agent comprises inosine as the effective ingredient, and a method for promoting the opening of flowers which method comprises the step of applying such flower-opening promoting agent to a plant at an appropriate time before its flower-opening, the time being determined depending on each target plant.

DETAILED DESCRIPTION OF THE INVENTION

The following will explain the present invention in detail.

The plants to which the flower-opening promoting agent of the present invention is to be applied include widely a persimmon and other fruit trees which blossom and bear fruits, fruit vegetables such as a strawberry, an eggplant, a tomato and the like from which fruits are harvested, various flowers of woody plants and herbs for the ornamental purpose, such as natural or fresh flowers.

Inosine is not necessarily needed to be a purified product. Insofar as it is free from adverse effects such as salt damage, inosine can be in the form of an inosine fermentation broth per se, a concentrate or a concentrated and dried product thereof, a crude product of inosine separated from an inosine fermentation broth, an inosine-containing intermediary treated fraction during obtaining a nucleic-acid related substance (nucleotides, nucleosides, nucleic acid bases, etc.) through decomposition of nucleic acid, an inosine-containing fraction of a processed inosinic acid fermentation broth or the like.

The flower-opening promoting agent for plants of the present invention containing inosine as the effective ingredient can be formed into a liquid preparation in which the promoting agent has been optionally dissolved or dispersed in a suitable solvent such as water or the like, upon its application. Moreover, it is possible to render such a liquid preparation pH 8 to 12 by adding an alkali having a preservative effect. Furthermore, it is also possible to form a powder preparation by using a proper diluent, filler, binder or the like. In this case, for example, when it is used for a strawberry, it is necessary to apply directly to its new shoots, and at that time, it is not preferred for the powdery diluent to remain at the growing points indefinitely. The same sometimes applies to fruit trees. Therefore, in such cases, it is necessary to give up the use of the diluent or to select a diluent.

The method for promoting the opening of flowers of the present invention aims to assist male and female flowers in opening in the sound and complete state at the flowering time. The time of the application of the flower-opening promoting agent for plants according to the present invention varies depending on the target plants.

Specifically, regarding fruit trees such as a persimmon, the time is about one month prior to the expected flowering time. In the case of a strawberry, it would be shorter than one month. At the time when a set of strawberry is raised, flower buds can be observed in the depth of the set on microscope, and the buds grow to flowering when a certain period of time has passed since final transplantation. The period is one month at the longest. Accordingly, in the case of applying to a strawberry for the aforementioned purpose, the time is about half a month prior to the expected flowering time. In the work for bearing flowers of Japanese Higan-sakura cherry or a forsythia for natural or fresh flowers, the plant is once placed in a high humidity hothouse for about one week to sprout flower buds and then taken out of the room. When the flower-opening promoting agent for plants of the present invention is used, flowers can be borne by spraying the flower-opening promoting agent of the present invention onto branches having young flower buds on the first day of taking the plant out of the room.

In greater detail, the flower buds grown to a size of rice grain usually bloom in a period of about two weeks, but upon the application of the flower-opening promoting agent for plants of the present invention, excellent and bright-colored large flowers appear in a half of the period, i.e., about one week. According to the present invention, as in this case, flower-opening is promoted and, in addition, bright-colored large flowers appear. With respect to Japanese Higan-sakura cherry, in the case of applying the flower-opening promoting agent for plants in solution of the present invention only to the base of a cut tree without applying onto the flower buds which begin to sprout, promotion of flower-opening is similarly observed but the flower color sometimes becomes pink. In the case of a forsythia, upon spraying the flower-opening promoting agent for plants of the present invention onto branches at which flower buds begin to sprout after being taken out of the hothouse, the flower-opening is promoted and flowers are large and voluminous.

Thus, application time varies with target plants, but those skilled in the art can easily determine the appropriate time for application, i.e., how many days before the expected flowering time in a particular case, with reference to the description of the present specification or by carrying out preliminary experiments.

Furthermore, the application method can be any method which can attach inosine, the effective ingredient, onto the flower buds of a plant, and the examples include spraying, dipping, coating and the like, but the method is not limited thereto. In the case of natural or fresh flowers, the promoting agent can be added to an aqua for natural or fresh flowers and then absorbed from the cut end of the base.

Proper application rate or amount varies with the kind of the target plant or the cultivation density in the case of a fruit plant or the like. It is noted that the flower-opening promoting agent for plants of the present invention is used in such amount that the flower-opening of the target plant is more promoted in degree of flowering than that of a plant cultivated under the same conditions except that the flower-opening promoting agent for plants of the present invention has not been applied. Such amount can be determined by some preliminary comparative tests which can be easily carried out by those skilled in the art. For example, it would range from the amount at which the target part is wetted, to the amount at which waterdrops fall, upon application with a power-driven sprayer. Like, in this case where the promoting agent is in the liquid form or a liquid preparation, the inosine concentration upon application can be, for example, from 20 to 100 ppm, preferably 40 to 80 ppm. In the case of Japanese Higan-sakura cherry described later in Example 2, an aqueous inosine solution having a concentration of about 60 ppm is sprayed three times a day with a power-driven sprayer, and at that time, the branches are bundled and placed in a water-inpoured bucket, so that the excessive inosine solution goes down the branches and is collected in the bucket. In such a manner, inosine is not only applied to the rice grain-shaped flower buds but also absorbed from the roots.

Finally, the meaning of "flower-opening promotion" according to the present invention is additionally noted. The words "flower-opening promotion" are generally understood only as meaning of "hastening flowering". In the market, however, contribution to bringing up flowers having sound and large stamens and pistils may be sometimes more important. For example, in the case of cherry blossoms for flower arrangement, much earlier flowering time becomes one merit and at the same time, blooming of excellent flowers is a factor of raising the market value. Regarding a strawberry and the like, early flowering is not so important but appearance of vigorous large flowers is requested. The flower-opening promoting agent for plants of the present invention can not only hasten the flowering time but also bring excellent flowers, so that "flower-opening promotion" according to the present invention means the flower-opening promotion in the broad sense covering both of "hasten flowering time" and "bring excellent flowers".

EXAMPLES

The following will explain the present invention in detail with reference to Examples.

Example 1

Japanese Fuyu-gaki Persimmon (Fruit Tree)

Regarding persimmons, if it rains at the flowering time, flower shells may remain attached. If the shells do not come off, good fruits cannot be obtained owing to facile creeping of gray mold (botulinus) or leafroller moths therein. On the contrary, their early coming off is an evidence of active cell division and progress of thickening or enlarging.

On April 25 of a certain year assumed to be one month before the flowering, the flower-opening promoting agent for plants of the present invention (an aqueous solution having an inosine concentration of about 60 ppm and containing potassium hydroxide) was applied by spraying to flower clusters before blossoming only at a limited part (an applied plot) of an adult tree of Japanese Fuyu-gaki persimmon (the height 2.5 m; the age: 25 years), while the other part was allowed to remain unsprayed as the control plot. The tree blossomed around May 20 and fruit bearing was observed. On June 1, it was recognized that only a smaller number of flower shells remained in the applied plot, flower shells being usually attached at the tips of the borne fruits. With respect to not only a persimmon but also an eggplant and a cucumber, it can be said that the early coming off of flower shells is an evidence of faster growth, because it is observed that when fruit bearing is sound and growth is active, the flower shells come off earlier. When flower shells remain indefinitely, it becomes a factor of fruit shedding owing to propagation of pathogenic bacteria therein. On September 30, in the autumn of the year, ten fruits remained in total and four fruits at the applied plot (test plot). The remaining six fruits at the control plot were borne dispersively. The test plot faced to the north but thickening or enlarging of the fruits were found to be better. Incidentally, although a typhoon struck on September 24, no fruits of the persimmon dropped at the test plot.

Example 2

Japanese Hiaan-sakura Cherry (Natural Flower for Decoration (Flower Arrangement))

Several branches of Japanese Higan-sakura cherry at which the flower buds began to sprout were taken out of a hothouse, placed in a bucket filled with water in an amount sufficient to soak the base of the branches, and sprayed with the same flower-opening promoting agent for plants of the present invention as used in Example 1 (an aqueous solution having an inosine concentration of about 60 ppm and containing potassium hydroxide) three times a day on the first day on which the plant was taken out of the hothouse.

As a result, the branches bloomed after only one week, though such branches bloom (therefore, are shipped) usually after two weeks in a bright room of a greenhouse. Moreover, not only early blooming was brought about but also cherry blossoms colored with a cherry color all over were obtained since it was possible to ship them before the formation of green calyxes under the flowers. Untreated cherry at the control plot was different in shape and color as if it were a different variety. If expressed, it had poor cherry blossoms without brightness. Incidentally, such difference being recognized, the treated cherry received an appreciation of a high market price.

As has been described above, according to the present invention, the flowering of Japanese Higan-sakura cherry for flower arrangement can be hastened and excellent flowers can be brought within a shorter period of time, and as a result, there is obtainable a merit that it is possible to ship it at the earliest time. In addition, by shipping both of plants treated with the flower-opening promoting agent for plants of the present invention and untreated plants having a usual flowering time, there can be also obtained a merit of extending a shipping term, i.e., capable of shipping for a longer period of time. The shipping at an earlier time and extension of shipping period are, needless to say, great boons to shipping persons.

Furthermore, since a forsythia has a longer demand period than Japanese Higan-sakura cherry has, and excellent yellow flowers are requested from December, a merit according to the present invention is as high as that in the case of Japanese Higan-sakura cherry.

[Effects of the Invention]

Fruit trees usually blossom and bear fruits excessively and undergo physiological fruit shedding. According to the present invention, it can be presumed that a sufficient amount of inosine is present at the time of flower bud formation before flowering and then the compound is immediately metabolized into various nucleotides and RNAs to form nucleic acids necessary for flower formation. Particularly, regarding fruit trees, after excessive flowering, physiological fruit shedding or manual fruit thinning is generally an ordinary matter. Namely, they prepare to leave offspring but reduce excessive fruits more than necessity according to their strength. As a matter of course, a meager fruit tree will finally abandon the flower buds in some cases, but usually a fruit tree maintains a durable number of fruits according to the tree vigor. Also in the case of fruit thinning, it is ordinary to leave fruits derived from pollinated sounder flower buds.

With respect to not only fruit trees but also grain crops such as a rice plant, it is, of course, significant to form sound flower buds. In addition, a plant hormone is used for bearing fruits regarding a melon and a tomato, but formation of sounder flower buds can be considered fundamentally.

In the case of the present invention, a means for growing more excellent fruits is sought through formation of more enriched flowers. The size of fruits mostly depends on the size of the flowers. For example, in the case of a strawberry, the number of the petals determines the size of the fruits. Usually, the number of the petals is five, but in the case of strong tree vigor with sound roots, the number becomes six, and the flowers having six petals result in a larger fruit certainly.

According to the present invention, sound flower buds can be formed and, as a result, fruits and decorative flowers of good quality can be provided.

What claimed is:

1. A method of promoting opening of flowers, which comprises the step of applying a flower-opening composition to a plant before flower opening, the composition comprising:
   a) an effective amount of inosine; and
   b) a carrier,
   wherein said effective amount is from 20 to 100 ppm.

2. The method of claim 1, wherein said carrier is water.

3. The method of claim 2, wherein said composition further contains an alkali substance, whereby the composition has a pH of 8 to 12.

4. The method of claim 3, wherein said alkali substance is potassium hydroxide.

5. The method of claim 2, wherein said flower-opening composition is applied to said plant up to about one month before flower opening.

6. The method of claim 5, wherein said flower-opening composition is applied to said plant up to about one-half of a month before flower opening.

7. The method of claim 1, wherein said composition is a powder, and said carrier is a filler.

8. The method of claim 1, wherein said flowers are flowers of fruits, vegetables, woody plants, herbs or ornamentals.

9. The method of claim 6, wherein said flowers are flowers of persimmon, strawberry, forsythia, cherry, rice, tomato or melon.

10. The method of claim 1, wherein said inosine is purified inosine.

11. The method of claim 1, wherein said inosine is in a form of a concentrate.

12. The method of claim 1, wherein said inosine is in a form of a crude product obtained from an inosine fermentation broth.

13. The method of claim 1, wherein said flower-opening composition is applied to said plant by spraying, dipping or coating.

14. The method of claim 1, wherein said plant is cut, and said flower-opening composition is contained in water and is absorbed by said plant through a cut end thereof.

15. The method of claim 14, wherein said cut plants are ornamentals.

16. The method of claim 1, wherein said inosine concentration is from 40 to 80 ppm.

17. A composition, comprising:
   a) about 20 to 100 ppm of inosine; in
   b) a liquid carrier,
   wherein the composition has a pH of 8 to 12.

18. The composition of claim 17, wherein said inosine is present in an amount of about 40 to 80 ppm.

19. The composition of claim 18, wherein said inosine is present in an amount of about 60 ppm.

20. The composition of claim 17, wherein said liquid carrier is water.

21. The composition of claim 17, further comprising potassium hydroxide.

* * * * *